(12) United States Patent
Konishi et al.

(10) Patent No.: US 8,679,547 B2
(45) Date of Patent: Mar. 25, 2014

(54) METHOD FOR MANUFACTURING CALCIUM SILICATE BASED COMPOSITION

(75) Inventors: Koh Konishi, Naruto (JP); Yuta Tsumura, Naruto (JP); Seiki Shinomiya, Naruto (JP); Masashi Konishi, Naruto (JP); Yukinori Konishi, Naruto (JP)

(73) Assignee: Tomita Pharmaceutical Co., Ltd., Naruto-shi (JP)

( * ) Notice: Subject to any disclaimer, the term of this patent is extended or adjusted under 35 U.S.C. 154(b) by 0 days.

(21) Appl. No.: 13/277,886

(22) Filed: Oct. 20, 2011

(65) Prior Publication Data

US 2013/0101685 A1  Apr. 25, 2013

(51) Int. Cl.
*A61K 33/06* (2006.01)
*C01B 33/24* (2006.01)

(52) U.S. Cl.
USPC .......................................... 424/682; 423/331

(58) Field of Classification Search
CPC ......... A61K 33/06; A61K 8/25; A61K 33/08; C01B 33/24; C01B 33/20
See application file for complete search history.

(56) References Cited

U.S. PATENT DOCUMENTS

| | | | |
|---|---|---|---|
| 2,742,345 A | * | 4/1956 | Hans Kohl et al. ............ 423/131 |
| 3,784,392 A | * | 1/1974 | Bertorelli ...................... 106/468 |
| 3,794,505 A | * | 2/1974 | Heiser et al. ................... 106/711 |
| 4,226,636 A | | 10/1980 | Mizutani et al. |
| 2003/0138369 A1 | | 7/2003 | Withiam et al. |

FOREIGN PATENT DOCUMENTS

| | | |
|---|---|---|
| JP | S54-93698 A | 7/1979 |
| JP | S55-32753 A | 3/1980 |
| JP | S55-85445 A | 6/1980 |
| JP | S56-5317 A | 1/1981 |
| JP | 4431391 B2 | 3/2010 |

OTHER PUBLICATIONS

Ray, A., "Hydrothermally treated cement-based building materials. Past, present, and future", Pure Appl. Chem., vol. 74, No. 11, pp. 2131-2135, 2002.*
Baltakys, K. et al., "The Influence of Stirring and γ-Al2O3 or Na2O Additives on the Gyrolite Formation in the CaO-Quartz-H2O System", Ceramics 51 (2) pp. 106-111 (2007).*

* cited by examiner

*Primary Examiner* — Tracy Vivlemore
*Assistant Examiner* — Monica Shin
(74) *Attorney, Agent, or Firm* — Fox Rothschild LLP

(57) ABSTRACT

Provided is a method that enables a calcium silicate-based material to be produced more efficiently. The method of producing a calcium silicate-based material comprises: (1) a step of obtaining a reaction product by reacting raw materials containing a calcium component, a silicon component and an aluminum component in an aqueous medium; and (2) a step of forming calcium silicate by subjecting the reaction product to hydrothermal treatment.

2 Claims, 3 Drawing Sheets

METHOD FOR MANUFACTURING CALCIUM SILICATE BASED COMPOSITION

BACKGROUND OF THE INVENTION

1. Field of the Invention

The present invention relates to a novel method of producing a calcium silicate-based material.

2. Description of the Related Art

Calcium silicate is used in various applications, including not only pharmaceuticals and food additives, but also molding assistants and insulating materials. A known example of a typical production method of calcium silicate is a production method of calcium silicate or a calcium silicate-gypsum complex including a reaction step of mixing and reacting gypsum and an alkaline silicate in an aqueous medium, a washing step of washing a solid fraction obtained in the reaction step, a slurry step of converting the solid fraction obtained in the washing step to a slurry, a hydrothermal treatment step of carrying out hydrothermal treatment on the slurry solution obtained in the slurry step, and a separation step of separating the calcium silicate or calcium silicate-gypsum complex obtained in the hydrothermal treatment step (Japanese Patent Application Publication No. S56-5317). Other methods for producing calcium silicate according to various conditions have also been proposed (Japanese Patent Application publication Nos. S55-85445, S55-32753 and S54-93698).

Since calcium silicate produced by a method like that described above has particularly large bulk specific volume and oil absorption, it can be used, for example, as an additive for preventing adhesion or improving fluidity of dehumidifying agents, a carrier for impregnating a liquid substance and the like, a molding assistant or an adsorbent. In particular, calcium silicate has been proposed for used in the formulation of pharmaceuticals due to its specific aspect ratio and high oil absorption (Japanese Patent No. 4431391).

However, there is still room for improvement of conventional methods used to produce calcium silicate with respect to conditions of the hydrothermal synthesis reaction (and particularly, with respect to the temperature and duration thereof). Namely, although being able to synthesize calcium silicate in a shorter period of time and at a lower temperature would make it possible to contribute to production on an industrial scale, such technology has yet to be developed.

SUMMARY OF THE INVENTION

Thus, a primary object of the present invention is to provide a method that enables a calcium silicate-based material to be produced more efficiently. In addition, another object of the present invention is to provide a calcium silicate-based material having high levels of bulk specific volume and oil absorption.

As a result of conducting extensive studies in consideration of the problems of the related art, the inventors of the present invention found that the above-mentioned objects can be achieved by employing a specific method, thereby leading to completion of the present invention.

Namely, the present invention relates to a production method of a calcium silicate-based material as described below.

1. A method of producing a calcium silicate-based material, comprising:
   (1) a step of obtaining a reaction product by reacting raw materials containing a calcium component, a silicon component and an aluminum component in an aqueous medium; and
   (2) a step of forming calcium silicate by subjecting the reaction product to hydrothermal treatment.

2. The production method described in 1 above, wherein at least one type of aluminum compound selected from the group consisting of an aluminum salt, an aluminum hydroxide and an aluminum oxide is used for a supply source of the aluminum component.

3. The production method described in 2 above, wherein the aluminum compound is at least one type selected from the group consisting of sodium aluminate, aluminum chloride and aluminum hydroxide.

4. The production method described in 1 above, wherein the calcium silicate contains gyrolite calcium silicate crystals.

5. The production method described in 1 above, wherein the molar ratio of $Al_2O_3/SiO_2$ in the raw materials is 0.002 or more.

6. The production method described in 1 above, wherein the hydrothermal treatment is performed under conditions of a temperature of 150° C. to 250° C. and a time of 1 to 4 hours.

7. A calcium silicate-based material containing an aluminum component, wherein the calcium silicate-based material has:
   (1) a bulk specific volume of 8 mL/g or more and an oil absorption of 2.5 mL/g or more; and
   (2) an aluminum content of 0.1% by weight to 1.0% by weight.

8. The calcium silicate-based material described in 7 above, which contains gyrolite calcium silicate crystals.

9. The calcium silicate-based material described in 7 above, wherein the specific surface area is 120 $m^2/g$ or more.

10. A pharmaceutical composition including the calcium silicate-based material described in 7 above.

Advantages of the Invention

According to the production method of a calcium silicate-based material of the present invention, a calcium silicate-based material can be efficiently produced by adding an aluminum component to the raw materials. In particular, calcium silicate-based material having high levels of bulk specific volume and oil absorption can be produced at a lower temperature and/or in a shorter period of time in a hydrothermal treatment step.

The calcium silicate-based material of the present invention has higher levels of bulk specific volume and oil absorption. In addition, specific surface area is also comparatively large. Consequently, the calcium silicate-based material of the present invention can be used in various applications as indicated below by taking advantage of these characteristics.

(1) Adhesion Prevention and Fluidity Improvement of Dehumidifying Agents

The calcium silicate-based material of the present invention can be used to produce composite particles such as calcium chloride by utilizing the high liquid absorption and moldability thereof. In this case since moisture absorbed by calcium chloride can be incorporated in the calcium silicate-based material, there is hardly any wetting of the particle surfaces and it is possible to maintain a dry state.

(2) Carrier Impregnation of Liquid Substances

In the case of impregnating a liquid such as a fragrance into a formed body (including granules) of the calcium silicate-based material of the present invention, the fragrance and the like can be sustained for a long period of time due to the large amount of liquid absorbed.

(3) Conversion of Liquids to Powders

Since the calcium silicate-based material of the present invention has a comparatively large pore volume, it is suitable for use in converting liquids having a high viscosity in particular to a powder. For example, it can be preferably used to convert not only the previously described liquid fragrance, but also liquid nutrient agents (such a vitamin E) or liquid antistatic agents and the like to powders.

(4) Molding Assistant

The calcium silicate-based material of the present invention can be preferably used as a molding assistant in the production of granules of solid bath agents or adsorbents and the like.

(5) Various Additives

The calcium silicate-based material of the present invention can be used as a carrier for solidifying liquid substances such as vitamins and other liposoluble drugs or liquid substances obtained by dissolving solid drugs. In addition, the calcium silicate-based material of the present invention can be used as a controlled-release additive (vehicle) for controlling the release (release rate) of an active ingredient, as well as a fluidity improver, pH adjuster or stabilizer and the like.

DESCRIPTION OF THE PREFERRED EMBODIMENTS

Figure 1:
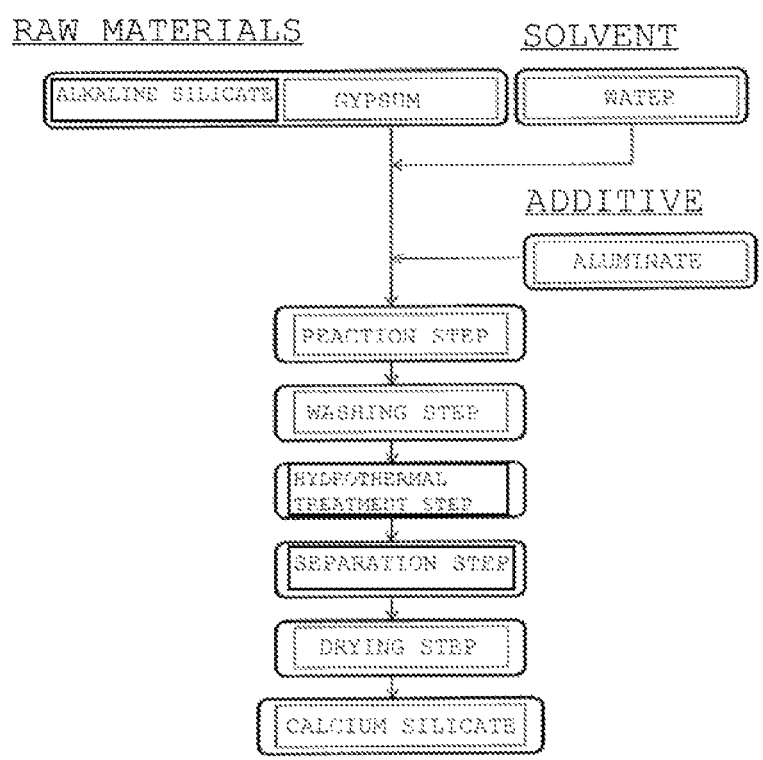
FIG. 1 is a drawing showing an example of the steps of the production method of the present invention.

1. Production Method of Calcium Silicate-Based Material

The production method of a calcium silicate-based material of the present invention comprises:

(1) a step of obtaining a reaction product by reacting raw materials containing a calcium component, a silicon component and an aluminum component in an aqueous medium (reaction step); and (2) a step of forming calcium silicate by subjecting the reaction product to hydrothermal treatment (hydrothermal treatment step).

Reaction Step

In the reaction step, a reaction product is obtained by reacting raw materials containing a calcium component, a silicon component and an aluminum component in an aqueous medium.

At least one type of aqueous medium selected from the group consisting of water and a water-soluble organic solvent can be used for the aqueous medium. Examples of water-soluble organic solvents that can be used include alcohol such as methanol, ethanol or propanol, and acetone or the like. In the present invention, water is used particularly preferably. There are no particular limitations on the amount of water used, and normally the amount of water used is suitably adjusted so that the solid fraction concentration of the raw materials is about 1% by weight to 25% by weight.

The raw materials consist of a calcium component, a silicon component and an aluminum component. Compounds serving as supply sources of these components can be used for each component.

A calcium compound serving as a supply source of the calcium component can be used for the calcium component. Examples of calcium compounds that can be used include calcium salts, calcium hydroxides and calcium oxides. Calcium salts such as calcium salts such as sulfates, chlorides, nitrates, carbonates or phosphates of calcium can be used particularly preferably. Specific examples thereof include calcium sulfate (or gypsum) and calcium chloride. In the present invention, water-soluble calcium compounds are used preferably.

A silicon compound serving as a supply source of the silicon component can be used for the silicon component. Examples of silicon compounds that can be used preferably include silicates such as sodium silicate or potassium silicate. In the present invention, water-soluble silicon compounds are used preferably.

An aluminum compound serving as a supply source of the aluminum component can be used for the aluminum component. Examples of the aluminum compounds include at least one type selected from the group consisting of aluminum salts, aluminum hydroxides and aluminum oxides. More specifically, at least one type of aluminum compound selected from the group consisting of sodium aluminate, aluminum chloride and aluminum hydroxide can be used preferably.

The blending ratio of the raw materials with respect to the calcium component and silicon component in particular is such that the resulting composition thereof is represented by calcium silicate ($2CaO.3SiO_2.mSiO_2.nH_2O$ (wherein, $1 \leq m \leq 2$, $2 \leq n \leq 3$)). Thus, the molar ratio of Ca/Si is preferably set within the range of about 0.4 to 0.5.

With respect to the aluminum component, the molar ratio of $Al_2O_3/SiO_2$ in the raw materials is preferably 0.002 or more, and in particular, the raw materials are more preferably blended so that the above-mentioned molar ratio is 0.003 or more. Furthermore, although the upper limit of the above-mentioned $Al_2O_3/SiO_2$ molar ratio can be suitably set corresponding to the application of the calcium silicate and the like, it is normally about 0.04.

An additive in the form of a pH adjuster (such as sodium hydroxide) can be suitably incorporated in the raw materials as necessary.

The raw materials added in the prescribed blending ratios are mixed in an aqueous medium and allowed to react. Although the reaction temperature in this case is not limiting, it is preferably set to, for example, 5° C. to 100° C., and particularly to within the range of 5° C. to 25° C. The reaction time can be suitably adjusted corresponding to the reaction temperature and the like. A reaction product can be obtained from the above-mentioned raw materials in this manner.

The resulting reaction product can also be rinsed with water prior to hydrothermal treatment as necessary. A method similar to a known method may be used to rinse (wash) the reaction product, and for example, a method can be employed in which the reaction product is subjected to solid-liquid separation followed by rinsing with water. The method used for solid-liquid separation is not limiting, and a known method such as filtration or centrifugal separation may be used. The above-mentioned rinsing can also be carried out repeatedly.

Hydrothermal Treatment Step

In the hydrothermal treatment step, calcium silicate (and particularly, crystalline calcium silicate) is prepared by subjecting the above-mentioned reaction product to hydrothermal treatment.

An aqueous medium may be added to the reaction product to form a slurry at the time of hydrothermal treatment. An aqueous medium such as any of the previously exemplified aqueous media can be used for the aqueous medium in this case. Although there are no particular limitations on the solid fraction concentration of the slurry, it is normally 1% by weight to 15% by weight and preferably about 3% by weight to 10% by weight.

Hydrothermal treatment can be carried out using a known device such as an autoclave. The reaction temperature is normally within the range of 150° C. to 250° C. The duration of hydrothermal treatment is an amount of time that is adequate for forming the prescribed crystalline calcium silicate. With respect to the temperature and time of the hydrothermal treatment in the present invention, by incorporating an aluminum component in the raw materials, a calcium silicate-based material having high bulk specific volume and oil absorption can be prepared at a lower temperature and in a shorter period of time. In other words, reacting at the same temperature for the same amount of time allows the obtaining of a calcium silicate-based material having higher levels of bulk specific volume and oil absorption.

2. Calcium Silicate-Based Material

The present invention also includes a calcium silicate-based material containing an aluminum component, wherein the calcium silicate-based material has:

(1) a bulk specific volume of 8 mL/g or more and an oil absorption of 2.5 mL/g or more; and (2) an aluminum content of 0.1% by weight to 1.0% by weight. A calcium silicate-based material obtained according to the production method of the present invention in particular can be used preferably for this type of calcium silicate-based material.

The calcium silicate-based material of the present invention has bulk specific volume of 8 mL/g or more and preferably 10 mL/g or more. In addition, the calcium silicate-based material of the present invention has oil absorption of 2.5 mL/g or more and preferably 2.5 mL/g or more.

The calcium silicate-based material of the present invention contains calcium silicate and an aluminum component, and is substantially preferably composed of calcium silicate and an aluminum component containing in calcium silicate.

Although the content of aluminum in the calcium silicate-based material can be suitably set corresponding to the application or usage method and the like of the calcium silicate, it is normally 0.1% by weight or more and preferably 0.2% by weight or more. Furthermore, the upper limit of the aluminum content is about 1.0% by weight.

The calcium silicate-based material of the present invention contains calcium silicate crystals, and more preferably contains gyrolite calcium silicate crystals. Gyrolite calcium silicate crystals in particular are composed of rose flower petal-shaped particles formed by aggregation of thin flakes, thereby making it possible to achieve the desired levels of bulk specific volume and oil absorption.

The calcium silicate-based material of the present invention is normally in the form of a powder, and the average particle diameter thereof is within the range of 1 μm to 100 μm and preferably within the range of 10 μm to 40 μm.

Although there are no particular limitations on the specific surface area of the calcium silicate-based material of the present invention, it is preferably 120 m²/g or more, more preferably 120 m²/g to 200 m²/g and most preferably 120 m²/g to 180 m²/g. Specific surface area of the present invention indicates a value obtained by measuring 0.02 g sample of a powder of the calcium silicate-based material of the present invention according to the multipoint BET method using the measuring device and under the pretreatment and test conditions indicated below.

Measuring device: High-speed specific surface area and pore size distribution measuring device (NOVA-4000e, Quantachrome Corp.)

Pretreatment conditions: Holding for 1 hour at 105° C. while degassing

Test conditions: Measuring with the 3-point plot method according to the nitrogen adsorption method (relative pressure: 0.1, 0.2, 0.3)

The pH (5% SUS) of the calcium silicate-based material of the present invention is normally alkaline, and more particularly, is 8 or higher and preferably 8.5 to 9.5. The pH in this case is the value obtained by measuring the pH of a liquid in which 2.5 g of sample are suspended in 50 mL of water with a pH meter.

The calcium silicate-based material of the present invention is characterized by having comparatively large pores in the case the calcium silicate is substantially composed of flower petal-shaped gyrolite calcium silicate crystals as previously described. As a result, differing from pores formed between aggregated particles of amorphous silicic anhydride, the calcium silicate-based material of the present invention is able to demonstrate high levels of liquid absorption or liquid retention properties and the like. For example, even in the case of having compression molded the calcium silicate-based material of the present invention into tablets, as a result of having large pores as described above, the resulting tablets are able to demonstrate high levels of liquid absorption or liquid retention properties and the like. The mean pore size of such a structure is normally about 6 nm to 100 nm. In addition, the pore volume is about 0.1 cc/g to 6.0 cc/g.

3. Pharmaceutical Composition

The present invention also includes a pharmaceutical composition containing the calcium silicate-based material of the present invention. The calcium silicate-based material of the present invention can be used not only as, for example, a vehicle, molding assistant or stabilizer, but also as a carrier of a liquid substance obtained by dissolving a liquid drug or solid drug. Thus, the calcium silicate-based material of the present invention can be used preferably in the case of formulating into tablets, for example. In addition, by loading an active ingredient into the pores of the calcium silicate-based material of the present invention, elution and gradual release of the active ingredient can be arbitrarily controlled.

There are no particular limitations on active ingredients (pharmaceutically active ingredients) that can be used in the pharmaceutical composition of the present invention, and any known or commercially available active ingredient can be used. Examples of active ingredients that can be used include hyperlipemia drugs, antiulcer drugs, antihypertensive drugs, antidepressants, antiasthmatic drugs, antiepileptic drugs, antiallergic drugs, antibacterial drugs, anticancer drugs, analgesics, anti-inflammatory drugs, antidiabetic drugs, antimetabolites, antagonists, osteoporosis drugs, antiplatelet drugs, antiemetic drugs, anesthetic drugs and hormone preparations.

Although the content of the calcium silicate-based material in the pharmaceutical composition of the present invention is not limiting, it can normally be suitably adjusted to within the range of 0.1% by weight to 99% by weight.

In addition, in the pharmaceutical composition of the present invention, a known pharmaceutical additive may also be contained in addition to the above-mentioned calcium silicate-based material and pharmaceutically active ingredient. Examples of pharmaceutical additives that can be used include excipients (such as lactose), disintegration agents (such as crospovidone or lowly substituted hydroxypropyl cellulose (L-HPC)), binders (such as methyl cellulose, ethyl cellulose, hydroxypropyl cellulose or hydroxypropyl cellulose), lubricants (such as magnesium stearate or calcium stearate), pH adjusters (such as citric acid, acetic acid, sulfuric acid, hydrochloric acid, lactic acid, sodium hydroxide or potassium hydroxide) and stabilizers (such as magnesium hydroxide, magnesium carbonate, magnesium oxide, calcium hydroxide, calcium carbonate, calcium oxide, hydrotalcite or hydrated silicon dioxide, magnesium aluminate metasilicate, magnesium silicate, calcium phosphate or calcium hydrogen phosphate). Although there are no particular limitations on the content of pharmaceutical additives provided it is within a range that does not impair the effects of the present invention, normally the content of pharmaceutical additives is preferably within the range of 0.1% by weight to 99% by weight.

The pharmaceutical composition can be applied in various drug forms. For example, the pharmaceutical composition may be in the form of a tablet, powder, capsule, granule, suspension or emulsion.

EXAMPLES

The following provides a more detailed explanation of characteristics of the present invention by indicating examples and comparative examples thereof. However, the scope of the present invention is not limited to the examples.

Example 1

A calcium silicate-based material was prepared according to the production flow shown in FIG. 1. First, 0.5 kg of gypsum dihydrate and 6.79 kg of water were placed in a reaction tank followed by stirring well to prepare a slurry. Next, 1.303 kg of JIS-3 sodium silicate and prescribed amounts of additives shown in sample nos. 2 to 6 and 9 to 11 of Table 1 (aluminum compound and sodium hydroxide) were added while stirring the slurry, followed by allowing to react while mixing the raw materials under atmospheric pressure at 20° C. to 25° C. (reaction step). The molar ratio of $CaSO_4/Na_2O.nSiO_2$ charged at this time was 1.06. Next, after filtering the reaction product, the reaction product was washed using water (washing step). Water was added to the resulting cake to prepare a slurry having a solid content of 5% by weight. This slurry was placed in an autoclave followed by carrying out hydrothermal treatment at the temperatures and times indicated in Table 1 with the autoclave sealed (hydrothermal treatment step). Following completion of hydrothermal treatment, the treated slurry was filtered and the resulting solid was dried for 24 hours at 105° C. (drying step). Powdered calcium silicate-based materials (sample nos. 2 to 6 and 9 to 11) were obtained in this manner.

As a result of analyzing the resulting samples by X-ray diffraction, all of the samples were confirmed to gyrolite calcium silicate. In addition, as a result of observing the samples with a scanning electron microscope, all of the samples were confirmed to be in the form of flower petals.

Comparative Example 1

A calcium silicate-based material was prepared according to the production flow shown in FIG. 1. First, 0.5 kg of gypsum dihydrate and 6.79 kg of water were placed in a reaction tank followed by stirring well to prepare a slurry. Next, 1.303 kg of JIS-3 sodium silicate and prescribed amounts of additives (aluminum compound and sodium hydroxide) shown in Table 1 (sample nos. 1, 7 and 8) were added while stirring the slurry, followed by allowing to react while mixing the raw materials under atmospheric pressure at 20° C. to 25° C. (reaction step). The molar ratio of $CaSO_4/Na_2O.nSiO_2$ charged at this time was 1.06. Next, after filtering the reaction product, the reaction product was washed using water (washing step). Water was added to the resulting cake to prepare a slurry having a solid content of 5% by weight. This slurry was placed in an autoclave followed by carrying out hydrothermal treatment at the temperatures and times indicated in Table 1 with the autoclave sealed (hydrothermal treatment step). Following completion of hydrothermal treatment, the treated slurry was filtered and the resulting solid was dried for 24 hours at 105° C. (drying step). Powdered calcium silicate-based materials (sample nos. 1, 7 and 8) were obtained in this manner.

Comparative Example 2

0.5 kg of gypsum dihydrate and 6.79 kg of water were placed in a reaction tank followed by stirring well to prepare a slurry. Next, 1.303 kg of JIS-3 sodium silicate and a prescribed amount of sodium hydroxide shown in Table 1 (sample no. 12) were added while stirring the slurry, followed by allowing to react while mixing the raw materials under atmospheric pressure at 20° C. to 25° C. (reaction step). The molar ratio of $CaSO_4/Na_2O.nSiO_2$ charged at this time was 1.06. Next, after filtering the reaction product, the reaction product was washed using water (washing step). Water was added to the resulting cake followed by the addition of 0.010 kg of aluminum hydroxide to prepare a slurry having a solid content of 5% by weight. This slurry was placed in an autoclave followed by carrying out hydrothermal treatment at the temperatures and times indicated in Table 1 with the autoclave sealed (hydrothermal treatment step). Following completion of hydrothermal treatment, the treated slurry was filtered and the resulting solid was dried for 24 hours at 105° C. (drying step). A powdered calcium silicate-based material (sample no. 12) was obtained in this manner.

TABLE 1

| | Raw Materials | | | Additives Na aluminate, Na hydroxide (kg) | | Hydrothermal Treatment | | Physical Properties | |
| --- | --- | --- | --- | --- | --- | --- | --- | --- | --- |
| No. | JIS-3 sodium silicate (kg) | Gypsum dihydrate (kg) | Water (kg) | | Al (%) | Temp. (° C.) | Time (h) | Bulk (ml/g) | Oil absorption (ml/g) |
| 1 | 1.303 | 0.5 | 6.79 | Al—Na* 0 NaOH 0.127 | 0.0058% | 200 | 3 | 7.35 | 2.5 |
| 2 | 1.303 | 0.5 | 6.79 | Al—Na 0.010 NaOH 0.122 | 0.10% | 200 | 3 | 11.77 | 3.4 |
| 3 | 1.303 | 0.5 | 6.79 | Al—Na 0.014 NaOH 0.120 | 0.15% | 200 | 3 | 12.15 | 3.4 |

TABLE 1-continued

| No. | Raw Materials JIS-3 sodium silicate (kg) | Gypsum dihydrate (kg) | Water (kg) | Additives Na aluminate, Na hydroxide (kg) | Al (%) | Hydrothermal Treatment Temp. (°C.) | Time (h) | Physical Properties Bulk (ml/g) | Oil absorption (ml/g) |
|---|---|---|---|---|---|---|---|---|---|
| 4 | 1.303 | 0.5 | 6.79 | Al—Na 0.019 NaOH 0.117 | 0.19% | 200 | 3 | 12.99 | 2.9 |
| 5 | 1.303 | 0.5 | 6.79 | Al—Na 0.029 NaOH 0.112 | 0.38% | 200 | 3 | 15.39 | 3.6 |
| 6 | 1.303 | 0.5 | 6.79 | Al—Na 0.049 NaOH 0.096 | 0.60% | 200 | 3 | 15.00 | 3.4 |
| 7 | 1.303 | 0.5 | 6.79 | Al—Na 0.096 NaOH 0.056 | 1.4% | 200 | 3 | 5.7 | 2.5 |
| 8 | 1.303 | 0.5 | 6.79 | Al—Na 0 NaOH 0.127 | 0.01% | 200 | 4 | 8.6 | 4.6 |
| 9 | 1.303 | 0.5 | 6.79 | Al—Na 0.029 NaOH 0.112 | 0.23% | 200 | 4 | 14.3 | 5.0 |
| 10 | 1.303 | 0.5 | 6.79 | AlOH 0.010 NaOH 0.127 | 0.4% | 200 | 3 | 13.5 | 3.6 |
| 11 | 1.303 | 0.5 | 6.79 | Al chloride hexahydrate 0.031 NaOH 0.127 | 0.1% | 200 | 3 | 10.8 | 3.6 |
| 12 | 1.303 | 0.5 | 6.79 | AlOH 0.010 (added after washing) NaOH 0.127 | 0.13% | 200 | 3 | 8.8 | 2.1 |

*Al—Na represents sodium aluminate.

Test Example 1

Each of the samples obtained in the above-mentioned examples and comparative examples were measured for aluminum content, bulk specific volume and oil absorption. The results are shown in Table 1. Furthermore, measurement of aluminum content, bulk specific volume and oil absorption were carried out as described below.

(1) Aluminum Content

Aluminum content was measured according to the standard addition method using the measuring device and under the measuring conditions indicated below.

1.0 g of sample were accurately weighed followed by the addition of 30 mL of dilute hydrochloric acid, heating for 1 hour over a water bath, cooling and brining to a volume of 100 mL with ultrapure water. The liquid was filtered with quantitative filter paper (No. 5C) and the filtrate was used as a test solution. This test solution was measured for aluminum content according to the standard addition method using an ICP optical emission spectrometer.

Measuring device: Vista-PRO (Seiko Instruments Inc.)

Measuring conditions: Atmospheric argon-nitrogen

Internal standard Y

Al 396.152

Y 377.433

(2) Bulk Specific Volume 2.5 g of sample were weighed out and placed in a 50 mL graduated cylinder followed by tapping from a height of 4 cm at a rate of 100 times/250 seconds, measuring the volume of the powder and calculating bulk specific volume according to the equation shown below.

Bulk specific volume (mL/g)=Powder volume (mL)/ powder weight (g)

(3) Oil Absorption 1.0 g of sample were weighed out and placed on a black plastic sheet. 4 to 5 drops at a time of boiling linseed oil contained in a biuret were dropped onto the sample from above and adequately kneaded with the powder using a spatula at the time of each addition. Once the entire mixture become a clump in the form of a hard pate, the boiling linseed oil was kneaded one drop at a time, dropping was ended immediately before the mixture suddenly became soft with the addition of a single drop, and the amount of boiling linseed oil dropped onto the sample at that time was read followed by calculation of oil absorption according to the equation indicated below.

Oil absorption (mL/g)=Volume of boiling linseed oil dropped onto sample (mL)/sample weight (g)

Test Example 2

Figure 2:
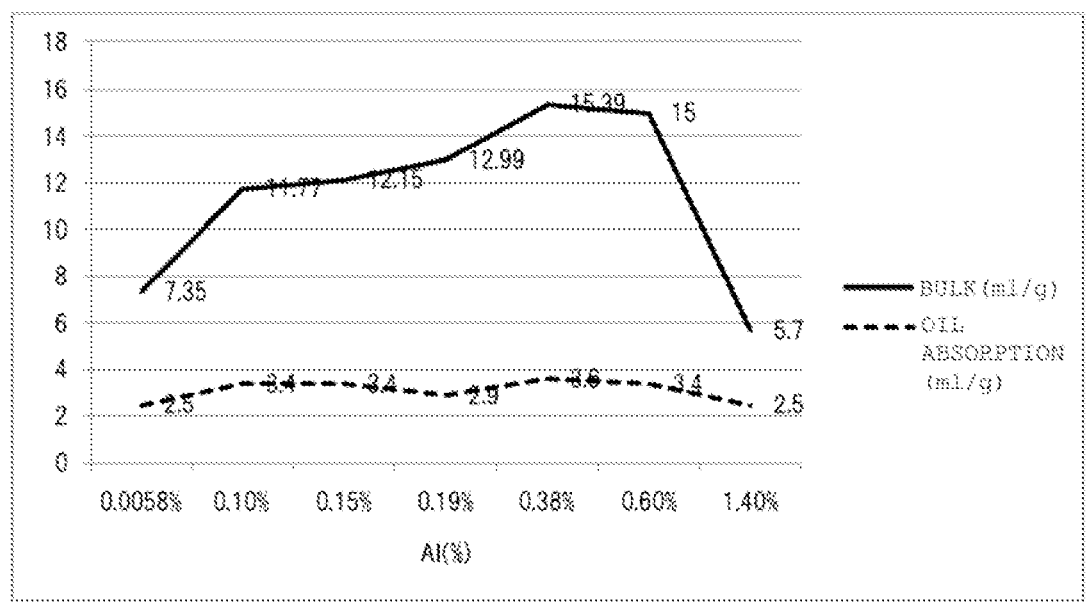
FIG. 2 is a graph showing the results of investigating the effects of an added amount of an aluminum component on bulk specific volume and oil absorption.

Each of the samples of the above-mentioned examples and comparative examples were investigated for the relationship between aluminum content and bulk specific volume or oil absorption. The results are shown in FIG. 2. As is clear from the results of FIG. 2, in the case of having added an aluminum component, both bulk specific volume and oil absorption were found to increase in comparison with the case of an aluminum content of 0.0058% by weight. In particular, that effect was found to be able to be demonstrated even at a comparatively small amount of aluminum component of 0.10% by weight to 0.60% by weight.

Test Example 3

Bulk specific volume and oil absorption were investigated for a sample (sample no. 9) prepared in the same manner as sample no. 5 of Example 1 with the exception of changing the conditions of hydrothermal treatment to 4 hours at 200° C.

Figure 3:
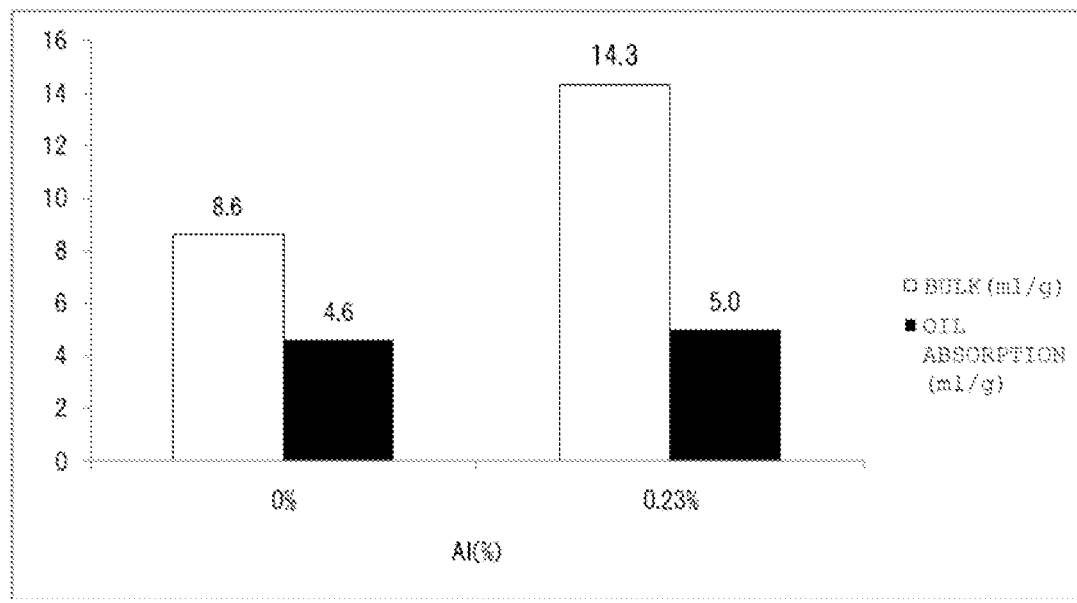
FIG. 3 is a graph showing the results of investigating the effects of an added amount of an aluminum component on bulk specific volume and oil absorption.

The results are shown in FIG. 3. Results for a sample to which an aluminum component was not added (sample no. 8) are also shown in FIG. 3. As is clear from the results of FIG. 3, a sample having an aluminum content of 0.23% by weight was found to demonstrate higher levels of bulk specific volume and oil absorption than a sample to which an aluminum component was not added.

Test Example 4

Values for pH, mean particle diameter, aluminum content and specific surface area and the like were investigated for the above-mentioned sample nos. 5 and 9. The results are shown in Table 2. Measurement results for samples to which an aluminum component was not added (sample nos. 1 and 8) are also shown in Table 2.

TABLE 2

|  | No. 1 | No. 8 | No. 5 | No. 9 |
| --- | --- | --- | --- | --- |
| Hydrothermal treatment temp. (° C.) | 200 | 200 | 200 | 200 |
| Hydrothermal treatment time (h) | 3 | 4 | 3 | 4 |
| pH (5%) | 9.18 | 8.79 | 9.19 | 9.01 |
| Bulk (mL/g) | 7.35 | 8.6 | 15.39 | 14.3 |
| Oil absorption (mL/g) | 2.5 | 4.6 | 3.6 | 5.0 |
| Specific surface area ($m^2/g$) | 53.8 | 118.6 | 133.1 | 171.2 |
| Mean particle diameter (μm) | 20.9 | 40.2 | 20.6 | 29.7 |
| Al (%) | 0.0058 | 0.01 | 0.38 | 0.23 |

As is clear from the results of Table 2, sample nos. 5 and 9 were found to demonstrate higher levels of bulk specific volume and oil absorption than the samples to which an aluminum component was not added, and specific surface area was also determined to be comparatively high within the range of 120 $m^2/g$ to 180 $m^2/g$.

What is claimed is:

1. A method of producing a calcium silicate-based material containing gyrolite calcium silicate crystals, comprising the steps of:
   (1) obtaining a reaction product by reacting raw materials containing a calcium component, a silicon component, and at least one aluminum component selected from the group consisting of sodium aluminate, aluminum chloride, and aluminum hydroxide in an aqueous medium; and
   (2) preparing calcium silicate by subjecting the reaction product to hydrothermal treatment under conditions of a temperature of 150° C. to 250° C. and a time of 1 to 4 hours.

2. The production method according to claim 1, wherein the calcium silicate-based material contains an aluminum component, and has:
   (1) a bulk specific volume of 8 mL/g or more and an oil absorption of 2.5 mL/g or more; and
   (2) an aluminum content of 0.1% by weight to 1.0% by weight.

* * * * *